United States Patent
Nagale et al.

(10) Patent No.: US 10,285,793 B2
(45) Date of Patent: May 14, 2019

(54) SURGICAL SCAFFOLDS

(71) Applicant: Boston Scientific Scimed Inc., Maple Grove, MN (US)

(72) Inventors: Sandra Nagale, Westford, MA (US); Mark W. Boden, Harrisville, RI (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 509 days.

(21) Appl. No.: 13/762,121

(22) Filed: Feb. 7, 2013

(65) Prior Publication Data

US 2013/0204077 A1 Aug. 8, 2013

Related U.S. Application Data

(60) Provisional application No. 61/596,303, filed on Feb. 8, 2012.

(51) Int. Cl.
| | |
|---|---|
| *A61F 2/00* | (2006.01) |
| *A61L 31/06* | (2006.01) |
| *A61L 31/14* | (2006.01) |
| *A61L 31/16* | (2006.01) |

(52) U.S. Cl.
CPC .......... *A61F 2/0063* (2013.01); *A61F 2/0045* (2013.01); *A61L 31/06* (2013.01); *A61L 31/146* (2013.01); *A61L 31/16* (2013.01); *A61F 2230/006* (2013.01); *A61L 2300/43* (2013.01); *A61L 2430/30* (2013.01); *A61L 2430/34* (2013.01); *F04C 2270/041* (2013.01)

(58) Field of Classification Search
CPC .................. A61F 2/0036; A61F 2/0077; A61F 2002/0068; A61F 2002/0081; A61F 2002/0086; A61F 2/0063; A61F 2/0045; A61L 2430/30; A61L 2430/34
See application file for complete search history.

(56) References Cited

U.S. PATENT DOCUMENTS

| | | | |
|---|---|---|---|
| 6,042,534 A * | 3/2000 | Gellman | A61F 2/0045 600/30 |
| 6,197,036 B1 | 3/2001 | Tripp et al. | |
| 7,824,462 B2 | 11/2010 | Webster et al. | |

(Continued)

FOREIGN PATENT DOCUMENTS

| | | |
|---|---|---|
| WO | 2002/019945 A2 | 3/2002 |
| WO | 2006/052695 A1 | 5/2006 |

(Continued)

OTHER PUBLICATIONS

Jing Lu et al., "Improved endothelial cell adhesion and proliferation on patterned titanium surfaces with rationally designed, micrometer to nanometer features", Acta Biomaterialia, vol. 4, Issue 1, Jan. 2008, pp. 192-201.

Megan Pattison et al., "Evaluating the In Vitro and In Vivo Efficacy of Nano-Structured Polymers for Bladder Tissue Replacement Applications", Macromolecular Bioscience, vol. 7, Issue 5, May 10, 2007, pp. 690-700.

(Continued)

*Primary Examiner* — Carrie R Dorna
(74) *Attorney, Agent, or Firm* — Brake Hughes Bellermann LLP (57) ABSTRACT

According to an aspect of the present invention, surgical scaffolds for soft tissue repair are provided. The surgical scaffolds comprise a sheet of a material within which through-holes are formed. Further aspects of the invention, among others, pertain to methods of using such surgical scaffolds and to kits containing such surgical scaffolds.

17 Claims, 3 Drawing Sheets

(56) References Cited

U.S. PATENT DOCUMENTS

| | | | |
|---|---|---|---|
| 7,975,698 B2* | 7/2011 | Browning | 128/834 |
| 8,506,582 B2* | 8/2013 | Kammerer et al. | 606/151 |
| 2003/0023137 A1* | 1/2003 | Gellman | A61F 2/0045 600/30 |
| 2004/0059356 A1 | 3/2004 | Gingras et al. | |
| 2004/0249473 A1 | 12/2004 | Delorme et al. | |
| 2005/0043820 A1 | 2/2005 | Browning | |
| 2007/0032695 A1* | 2/2007 | Weiser | A61F 2/0045 600/29 |
| 2009/0171143 A1 | 7/2009 | Chu et al. | |
| 2009/0171377 A1 | 7/2009 | Intoccia et al. | |
| 2009/0281558 A1 | 11/2009 | Li et al. | |
| 2009/0281635 A1 | 11/2009 | Li et al. | |
| 2010/0023104 A1 | 1/2010 | Desai et al. | |
| 2010/0179298 A1 | 7/2010 | Faust et al. | |
| 2011/0184228 A1 | 7/2011 | Sherry et al. | |
| 2011/0245589 A1* | 10/2011 | Palma | A61B 17/06109 600/30 |
| 2013/0178696 A1 | 7/2013 | Lotze et al. | |
| 2013/0330688 A1* | 12/2013 | Hedrick | A61L 17/04 433/173 |

FOREIGN PATENT DOCUMENTS

| | | |
|---|---|---|
| WO | 2007/014241 A1 | 2/2007 |
| WO | 2009/158600 A1 | 12/2009 |
| WO | 2010/052584 A2 | 5/2010 |
| WO | 2010/093333 A1 | 8/2010 |

OTHER PUBLICATIONS

Anil Thapa et al., "Nano-structured polymers enhance bladder smooth muscle cell function", Biomaterials 24, (2003) pp. 2915-2926.

Andrew Feola et al., "Impact of Pregnancy and Vaginal Delivery on the Passive and Active Mechanics of the Rat Vagina", Ann Biomed Eng., Jan. 2011, 39(1), pp. 549-558.

George Whiteside et al., "Molecular engineering of surfaces using self-assembled monolayers", Sci. Prog. 88 (2005), pp. 17-48.

Duma, et al., "A Computational Model of the Pregnant Occupant: Effects of Restraint Usage and Occupant Position on Fetal Injury Risk", Paper No. 05-0367, 19th International Technical Conference on the Enhanced Safety of Vehicles, 2005, 9 pages.

Shahryarinejad, et al., "Effect of hormone replacement and selective estrogen receptor modulators (SERMs) on the biomechanics and biochemistry of pelvic support ligaments in the cynomolgus monkey (*Macaca fascicularis*)", Am J Obstet Gynecol, vol. 202, Issue 5, May 2010, pp. 485.e1-485.e9.

Communication pursuant to Article 94(3) EPC for European Application No. 13706804.5, dated Nov. 15, 2017, 6 pages.

Pattison, et al, "Evaluating the In Vitro and In Vivi Efficacy of Nano-Structured Polymers for Bladder Tissue Replacement Applications", Macromolecular Bioscience, No. 7, 2007, pp. 690-700.

Thapa, et al, "Nano-structured polymers enhance bladder smooth muscle cell function", Biomaterials, Elsevier Science Publishers BV, Barking, GB, vol. 24, No. 17, Aug. 1, 2003, pp. 2915-2926.

* cited by examiner

SURGICAL SCAFFOLDS

STATEMENT OF RELATED APPLICATION

This application claims the benefit of U.S. Ser. No. 61/596,303, filed Feb. 8, 2012 and entitled "SURGICAL SCAFFOLDS," which is hereby incorporated by reference in its entirety.

FIELD OF THE INVENTION

The present invention relates generally to medical articles, and more particularly to scaffolds for surgical applications.

BACKGROUND

Pelvic floor disorders are highly prevalent among women. Estimates indicate that around 225,000 women require pelvic organ prolapse (POP) surgery each year in the U.S. and current projections show that one in three women will have to undergo POP surgery by 2050. Pelvic floor disorders involve a dropping down (prolapse) of the bladder, rectum, or uterus caused by weakness of or injury to the ligaments, connective tissue, and muscles of the pelvis. The different types of pelvic floor disorders are named according to the organ affected. For example, a rectocele develops when the rectum drops down and protrudes into the back wall of the vagina. An enterocele develops when the small intestine and the lining of the abdominal cavity (peritoneum) bulge downward between the uterus and the rectum or, if the uterus has been removed, between the bladder and the rectum. A cystocele develops when the bladder drops down and protrudes into the front wall of the vagina. In prolapse of the uterus (procidentia), the uterus drops down into the vagina. Pelvic floor disorders are commonly treated by implanting a surgical mesh within the patient's pelvis to support the organ or organs that require support.

Surgical meshes are also employed in various other soft tissue applications. As one example, urinary incontinence affects millions of men and women of all ages in the United States. Stress urinary incontinence (SUI) affects primarily women and is generally caused by two conditions, intrinsic sphincter deficiency (ISD) and hypermobility. These conditions may occur independently or in combination. In ISD, the urinary sphincter valve, located within the urethra, fails to close properly (coapt), causing urine to leak out of the urethra during stressful activity. Hypermobility is a condition in which the pelvic floor is distended, weakened, or damaged, causing the bladder neck and proximal urethra to rotate and descend in response to increases in intra-abdominal pressure (e.g., due to sneezing, coughing, straining, etc.). The result is that there is an insufficient response time to promote urethral closure and, consequently, urine leakage and/or flow results. A common treatment of SUI is via the use of a surgical mesh, commonly referred to as a sling, which is permanently placed under a patient's bladder neck or mid-urethra to provide a urethral platform. Placement of the sling limits the endopelvic fascia drop, while providing compression to the urethral sphincter to improve coaptation. Further information regarding sling procedures may be found, for example, in the following: Fred E. Govier et al., "Pubovaginal slings: a review of the technical variables," Curr. Opin. Urol. 11:405-410, 2001, John Klutke and Carl Klutke, "The promise of tension-free vaginal tape for female SUI," Contemporary Urol. pp. 59-73, October 2000; and PCT Patent Publication No. WO 00/74633 A2: "Method and Apparatus for Adjusting Flexible Areal Polymer Implants."

Ideally, materials for soft tissue repair, including SUI treatment and POP repair, will induce minimal foreign body response and promote healthy healing and remodeling. In this regard, materials with surface properties that enable adhesion of desired host cell types that induce favorable tissue remodeling are desired.

SUMMARY OF THE INVENTION

According to an aspect of the present invention, surgical scaffolds for soft tissue repair are provided, which comprise a sheet of polymeric material, wherein a plurality of through-holes are formed in the sheet. In various embodiments, at least one surface of the sheet is provided with surface features that promote cell adhesion and proliferation.

Further aspects of the invention, among others, pertain to methods of using such surgical scaffolds and to kits containing such surgical scaffolds.

These and other aspects, embodiments and advantages of the present invention will become immediately apparent to those of ordinary skill in the art upon review of the Detailed Description and any claims to follow.

DETAILED DESCRIPTION

A more complete understanding of the present invention is available by reference to the following detailed description of numerous aspects and embodiments of the invention. The detailed description of the invention which follows is intended to illustrate but not limit the invention.

According to an aspect of the present disclosure, surgical scaffolds for soft tissue repair are provided, which comprise a sheet of polymeric material, wherein a plurality of through-holes are formed in the sheet.

As used a "sheet" of material is one whose length and width are at least 10 times greater than its thickness, for example, one whose length and width are each 10 to 25 to 50 to 100 to 250 to 500 or more times the thickness.

Surgical scaffolds in accordance with the disclosure may be in the form of ribbons and other more complex shapes (see, e.g., FIGS. 1-3 and 5 herein, among numerous other possibilities). In certain embodiments, surgical scaffolds in accordance with the disclosure will be able to take on a planar configuration, for example, when placed on a planar surface such as a table top. However, surgical scaffolds in accordance with the disclosure need not be planar. For example, surgical scaffolds in accordance with the disclosure may curve in space.

Surgical scaffolds in accordance with the present disclosure include, for example, a wide variety of scaffolds for soft tissue repair, including scaffolds for pelvic floor repair, vaginal slings, scaffolds for renal pelvis repair, urethral slings, hernia scaffolds (e.g., scaffolds for inguinal hernia, hiatus hernia, etc.), scaffolds for thoracic wall defects, breast support scaffolds and various other soft-tissue surgical support devices, including scaffolds for cosmetic and reconstructive surgery, among others. Surgical scaffolds may be surgically implanted in a variety of subjects, typically vertebrate subjects, more typically mammalian subjects, including human subjects, pets and livestock.

Unlike woven meshes and non-woven meshes (including knitted meshes, felt meshes and spunbound meshes, among others), the scaffolds of the present disclosure are not formed from one or more filaments. Instead, the scaffold preferably comprises a sheet of non-filamentous material within which through-holes are formed. As discussed in more detail below, in some embodiments, the through-holes may be formed concurrently with the formation of the sheet (e.g., by molding). In some embodiments, the though holes may be formed subsequent to sheet formation, for example, by a suitable cutting operation (e.g., die cut, laser cut, water-jet cut, etc.) or by a perforation operation.

The holes formed in the scaffolds of the present disclosure have a number of effects on the properties of the scaffolds including the mechanical properties of the scaffolds and the capacity of the scaffolds to promote or resist tissue ingrowth, among other effects. With regard to mechanical properties, holes of various sizes, shapes and densities can be used to modify the elongation of the scaffolds under load (i.e., the Young's modulus of the scaffold). Consequently, the measured Young's modulus of scaffolds (referred to herein as "scaffold modulus") can differ from the Young's modulus of the materials making up the scaffolds (referred to herein as "material modulus"). Moreover, anisotropy can be provided to the scaffold modulus by varying hole size, shape and/or density along the surface of the scaffolds (e.g., by employing elongated holes).

Materials for forming scaffolds in accordance with the present disclosure include various synthetic biostable polymers, various synthetic biodisintegrable polymers, various naturally occurring biostable polymers and various naturally occurring biodisintegrable polymers. A combination of biostable and biodisintegrable polymers may be employed in certain embodiments. In certain embodiments, covalently crosslinked polymers may be employed (e.g., to increase stability, increase strength, etc.).

Examples of synthetic biostable polymers (which can yield permanent implants) may be selected from the following: (a) polyolefin homopolymers and copolymers, including homopolymers and copolymers of C2-C8 alkenes, for example, polyethylene and polypropylene among others, (b) fluoropolymers, including homopolymers and copolymers of C2-C8 alkenes in which one or more hydrogen atoms are substituted with fluorine, for example, polytetrafluoroethylene (PTFE), polyvinylidene fluoride (PVDF), poly(vinylidene fluoride-co-hexafluoropropene) (PVDF-HFP) among others, (c) polyamides such as nylons, among others, (d) polyesters, including, for example, polyethylene terephthalate, among others, (e) polyurethanes such as polyisobutylene based polyurethanes (PIB-PU) that comprise one or more polyisobutylene segments, among others, (f) polyoxyalkylenes including homopolymers of trioxane (polytrioxane, also known as polyoxymethylene or acetal) and copolymers of trioxane (e.g., copolymers of trioxane and dioxane), (g) styrenic copolymers such as alkene-styrene copolymers, including block copolymers comprising one or more polystyrene blocks and one or more polyalkene blocks, for instance, poly(styrene-b-isobutylene-b-styrene) (SIBS), poly(styrene-b-ethylene/butylene-b-styrene) (SEBS) among others, (h) as well as various other non-absorbable polymers and copolymers (including block copolymers).

Examples of synthetic biodegradable polymers may be selected, for example, from polyesters and polyanhydrides, among others. Specific biodegradable polymers may be selected from suitable members of the following, among others: (a) polyester homopolymers and copolymers (including polyesters and poly[ester-amides]), such as polyglycolide, polylactide (PLA), including poly-L-lactide, poly-D-lactide, and poly-D,L-lactide, poly(lactide-co-glycolide) (PLG), including poly(L-lactide-co-glycolide), poly(D-lactide-co-glycolide) and poly(D,L-lactide-co-glycolide), poly(beta-hydroxybutyrate), poly-D-gluconate, poly-L-gluconate, poly-D,L-gluconate, poly(epsilon-caprolactone), poly(delta-valerolactone), poly(p-dioxanone), poly(trimethylene carbonate), poly(lactide-co-delta-valerolactone), poly(lactide-co-epsilon-caprolactone), poly(lactide-co-beta-malic acid), poly(lactide-co-trimethylene carbonate), poly(glycolide-co-trimethylene carbonate), poly(beta-hydroxybutyrate-co-beta-hydroxyvalerate), poly[1,3-bis(p-carboxyphenoxy)propane-co-sebacic acid], poly(sebacic acid-co-fumaric acid), and poly(ortho esters) such as those synthesized by copolymerization of various diketene acetals and diols, among others; and (b) polyanhydride homopolymers and copolymers such as poly(adipic anhydride), poly(suberic anhydride), poly(sebacic anhydride), poly(dodecanedioic anhydride), poly(maleic anhydride), poly[1,3-bis(p-carboxyphenoxy)methane anhydride], and poly[alpha,omega-bis(p-carboxyphenoxy)alkane anhydrides] such as poly[1,3-bis(p-carboxyphenoxy)propane anhydride] and poly[1,6-bis(p-carboxyphenoxy)hexane anhydride], among others.

Where a biodegradable polyester is used (e.g., PLA, PLG, etc.), one or more soft blocks, for example, polyethylene oxide (PEO), poly(trimethylene carbonate) (PTMC), poly(dioxane-2-one) (PPDO) or polycaprolactone (PCL) blocks, among others, may be included with one or more polyester blocks in the polymer to vary hardness, elongation, and degradation rate of the polymer. Examples include diblock and triblock copolymers such as PLA-PCL, PLA-PCL-PLA, PLG-PCL, PLG-PCL-PLG, PLA-PEO, PLA-PEO-PLA, PLG-PEO, PLG-PEO-PLG, PCL-PLA-PTMC, PLA-PTMC-PCL and PLA-PTMC-PPDO, among others.

Where copolymers are employed, copolymers with a variety of monomer ratios may be available. For example, where isobutylene-styrene copolymers (e.g., SIBS) are used, the ratio of monomers in these polymers can be selected to obtain mechanical properties such that tissue compatibility is enhanced. For instance, a higher isobutylene content will result in a softer polymer that may be a better match for the durometer of the surrounding tissue. As another example, where PLG is used, a variety of lactide:glycolide molar ratios will find use herein, and the ratio is largely a matter of choice, depending in part on the rate of degradation desired. For instance, a 50:50 PLG polymer, containing 50% D,L- lactide and 50% glycolide, will provide a faster resorbing copolymer, while 75:25 PLG degrades more slowly, and 85:15 and 90:10, even more slowly, due to the increased lactide component. Degradation rate can also be controlled by such factors as polymer molecular weight and polymer crystallinity. More broadly, where used, PLG copolymers include those having a lactide/glycolide molar ratio ranging, for example, from 10:90 or less to 15:85 to 20:80 to 25:75 to 40:60 to 45:55 to 50:50 to 55:45 to 60:40 to 75:25 to 80:20 to 85:15 to 90:10 or more.

Examples of naturally occurring polymers include biostable and biodegradable polymers such as cellulose including biosynthesized cellulose, alginic acid, hyaluronic acid, and collagen, among many others.

Polymers employed herein include non-crosslinked and crosslinked (e.g., ionically crosslinked, covalently crosslinked, etc.) polymers.

The overall thickness of the surgical scaffolds of the present disclosure may range, in certain embodiments, from 50 µm or less to 75 µm to 100 µm to 150 µm to 200 µm to 250 µm to 300 µm to 400 µm to 500 µm or more, more typically from 100 µm to 250 µm.

In various embodiments, the surgical scaffolds of the present disclosure preferably have through-hole sizes ranging from 0.075 mm or less to 0.1 mm to 0.25 mm to 0.5 mm to 1 mm to 2.5 to 5 mm to 10 mm or more in width, more typically, ranging from 0.5 mm to 0.75 mm to 1 mm to 2 mm to 3 mm to 4 mm to 5 mm in width.

A wide variety of regular and irregular through-hole shapes may be employed in the scaffolds described herein including circular through-holes, oval through-holes and polygonal through-holes, among many others. Throughholes typically have at least one plane of symmetry, more typically two or more planes of symmetry. Through-holes typically have a surface aspect ratio (length divided by width) ranging from 1 to 1.5 to 2 to 5 or more.

Through-hole density (through-hole area divided by total scaffold area) can range, for example, from 1% or less to 90% or more (e.g., ranging from 1% to 2% to 5% to 10% to 25% to 50% to 75% to 90%).

Scaffolds in accordance with the present disclosure may have a wide range of mass densities (also sometimes referred to as surface density or mesh weight). In certain embodiments, the mass density ranges, for example, from 1 g/m$^2$ or less to 100 g/m$^2$ or more (e.g., ranging 1 g/m$^2$ to 2 g/m$^2$ to 5 g/m$^2$ to 10 g/m$^2$ to 15 g/m$^2$ to 20 g/m$^2$ to 25 g/m$^2$ to 50 g/m$^2$ to 75 g/m$^2$ to 100 g/m$^2$), more typically ranging from 1 g/m$^2$ to <20 g/m$^2$.

In various embodiments, scaffolds in accordance with the present disclosure contain surface features, such as surface nano-features, surface micro-features, or both. As used herein, "surface features" at topographic features which may be in the form of, for example, (a) depressions, such as holes (including through-holes, which extend through the scaffold, and blind holes, which do not extend through the scaffold) and trenches, (b) protuberances, such as pillars and ridges or (c) both. (Surfaces comprising topographic features in the form of waves can be considered as either series of ridges or a series trenches). Surface features may be molded, or they may be generated on a previously formed scaffold surface (e.g., by calandering, cutting, etching, etc.). Where trenches and/or ridges are present, they commonly include a series of trenches and/or ridges that are parallel to one another, and can further include two parallel sets that intersect one another in a cross-hatched-type pattern, for example, intersecting at an angle ranging from near-parallel up to perpendicular, for instance, intersecting at an angle ranging from 5° to 10° to 15° to 30° to 45° to 90°. Where depressions are present, they may be loaded with various additional agents (e.g., therapeutic agents, biopolymers, etc.) such as those described below.

Surgical scaffolds in accordance with the present disclosure may comprise surface nano-features. As used herein a "surface nano-feature" is a surface feature that has a lateral dimension (length or width), a vertical dimension (height or depth), or combination of dimensions (e.g., length and width; width and depth; length, width and depth; width and height; length, width and height; etc.) ranging from 1 to 1000 nm (e.g., from 1 nm to 2 nm to 5 nm to 10 nm to 25 nm to 50 nm to 100 nm to 250 nm to 500 nm to 750 nm to 1000 nm), preferably from 5 to 750 nm, more preferably 10 to 250 nm. Surface nano-features may be spaced from one another by a distance ranging, for example, from 1 to 1000 nm (e.g., from 1 nm to 2 nm to 5 nm to 10 nm to 25 nm to 50 nm to 100 nm to 250 nm to 500 nm to 750 nm to 1000 nm). In various embodiments, the spacing between features is on the same order of magnitude as the width of the features.

Surface nano-features may promote desired protein adsorption (e.g., fibrin, laminin and other proteins that induce cell adhesion and proliferation) leading to preferential adhesion of desirable cells such as macrophages, fibroblasts and epithelial cells (which can lead to NO production and extracellular matrix production), among others, as well as the rejection of undesirable cells such as bacteria. For example, nanotextured metal and polymer surfaces with nano-features (holes) have been shown to promote adhesion of desired proteins and cells that promote healing, while at the same time preventing infection. For further information, see, e.g., J. Lu et al., *Acta Biomaterialia*, Volume 4, Issue 1, January 2008, Pages 192-201, U.S. Pat. No. 7,824,462 to Webster et al., and M. Pattison et al., *Macromolecular Bioscience*, Volume 7, Issue 5, May 10, 2007, pages 690-700. Nanostructured polymer (e.g., polyurethane and PLGA) surfaces have been shown to enhance smooth muscle cell adhesion, proliferation, and the production of extracellular matrix (ECM) proteins in the human bladder. See A. Thapa et al., *Biomaterials* 24 (2003) 2915-2926.

Surgical scaffolds in accordance with the present disclosure may also comprise surface micro-features. As used herein a "surface micro-feature" is a surface feature that has a lateral dimension (length or width), a vertical dimension (height or depth), or combination of dimensions (e.g., length and width; width and depth; length, width and depth; width and height; length, width and height; etc.) ranging from 1 to 1000 µm (e.g., ranging from 1 µm to 2 µm to 5 µm to 10 µm to 25 µm to 50 µm to 100 µm to 250 µm to 500 µm to 750 µm to 1000 µm), preferably from 2 to 20 µm, in some embodiments. Surface micro-features may be spaced from one another by a distance ranging, for example, from 1 to 1000 µm (e.g., from 1 µm to 2 µm to 5 µm to 10 µm to 25 µm to 50 µm to 100 µm to 250 µm to 500 µm to 750 µm to 1000 µm). In various embodiments, the spacing between features is on the same order of magnitude as the width of the features.

Surface micro-features may prevent slippage and promote desired traction between the scaffold and adjacent tissue (e.g., the vaginal muscularis on anterior and posterior vaginal walls, connective tissue, etc.). Surface micro-features may also promote desirable cell proliferation and alignment.

Surfaces can be varied with one side being textured with nano-features and/or micro-features (for example, to promote one or more of protein adhesion, cell adhesion, cell growth, cell proliferation, cell alignment and tissue ingrowth) and the other side being smooth to prevent organ adhesions.

In various embodiments, scaffolds in accordance with the disclosure may undergo significant elongation under load. In this regard, A. Feola et al., *Ann. Biomed. Eng.* 39 (2011) 549-558 describes vaginal tissue as active, being able to generate a force, and passive, being able to transfer a force. The use of a highly rigid mesh which does not undergo significant elongation under load, for instance, constructed using a rigid material such as polypropylene (e.g., having a material Young's modulus of about 1500 N/mm$^2$) may lead to muscle atrophy since the mesh supplants the need or even the ability for the muscularis of the vagina to function normally.

It is further desirable in certain embodiments to employ a material that approximately matches the hardness (durometer) of internal tissue with which it comes into contact. For instance, in a pelvic floor repair scaffold like that described below, the body portion of the scaffold that contacts and supports the vagina may have a durometer ranging from, for example, 60A-100A, whereas the durometer of the arms may be significantly higher.

Scaffolds in accordance with the present disclosure can be tailored to provide anisotropic mechanical properties, for example, by varying the polymeric composition or by varying scaffolding thickness, varying through-hole density, varying through-hole shape (e.g., elongated holes having an aspect ratio of more than 1, more typically more than 2), by varying conditions during extrusion of the material, such as inducing a strain in one dimension during cooling in order to orient crystals in the material, or combinations of the preceding techniques. In this way, scaffolds can be provided which have one set of characteristic mechanical properties in a first direction and another set of mechanical properties in a second direction. For example, a scaffold may be provided which has lower elongation (and higher strength) in a first direction and higher elongation (and lower strength) in a second direction. In this regard, in some embodiments the Young's modulus in a first direction may at least 1.5 times greater (e.g., ranging from 1.5 times greater to 2 times greater to 3 times greater to 5 times greater or more) than the Young's modulus in a second direction (e.g., a direction that is perpendicular to the first direction).

For instance, various scaffolds are described herein for pelvic floor repair which have a body portion that is configured to wrap around and supports a subject's vagina and multiple arms that can be affixed for various support structures (e.g., ligaments) within the pelvis of the subject. In such scaffolds, the body portion can be provided with anisotropic properties which better mimic normal vaginal support structures. For example the body portion may be provided with lower elongation and higher strength properties (e.g., a scaffold Young's modulus ranging from >0.1 up to 100 N/mm$^2$) in a first direction that extends along the length of the vagina and higher elongation and lower strength properties (e.g., a scaffold Young's modulus ranging from 0.1 to <100 N/mm$^2$) in a second direction that extends around the circumference of the vagina. In certain embodiments, the scaffold Young's modulus in the first direction ranges from 1 to 5 times (e.g., 1.25 to 1.5 to 2 to 3 to 4 to 5 times) the scaffold Young's modulus in the second direction.

It is preferred that the scaffolds in these embodiments maintain the aspect ratio when strained. For example, current meshes prepared from a material with a high Young's modulus can be elongated in one direction, but typically shrink in the dimension perpendicular to the strain. By selection of the appropriate material, the mesh may be elongated in multiple directions at the same time, without shrinking or "necking" perpendicular to the strain.

In certain embodiments, the scaffolds of the present disclosure may comprise various additional agents (i.e., agents in addition to the polymeric material that is used to form the scaffold) including therapeutic agents, biopolymers and imaging agents, among other agents.

In certain embodiments, the scaffolds of the present disclosure comprise one or more therapeutic agents, for example, selected from the following, among many others: (a) hormones such as estrogen, and progesterone, (b) anti-inflammatory agents (e.g., for purposes of reducing macrophage levels, resulting in less muscle regeneration and re-growth and less scarring or fibrous capsule formation) including corticosteroids such as hydrocortisone and prednisolone, and non-steroidal anti-inflammatory drugs (NSAIDS) such as aspirin, ibuprofen, and naproxen; (c) narcotic and non-narcotic analgesics and local anesthetic agents (e.g., for purposes of minimizing pain); (d) growth factors such as epidermal growth factor and transforming growth factor-α (e.g., for purposes of stimulate the healing process and or promoting growth of collagenous tissue); (e) antibiotic agents such as the penicillins (e.g., penicillin G, methicillin, oxacillin, ampicillin, amoxicillin, ticarcillin, etc.), the cephalosporins (e.g., cephalothin, cefazolin, cefoxitin, cefotaxime, cefaclor, cefoperazone, cefixime, ceftriaxone, cefuroxime, etc.), the carbapenems (e.g., imipenem, metropenem, etc.), the monobactems (e.g., aztreonem, etc.), the carbacephems (e.g., loracarbef, etc.), the glycopeptides (e.g., vancomycin, teichoplanin, etc.), bacitracin, polymyxins, colistins, fluoroquinolones (e.g., norfloxacin, lomefloxacin, fleroxacin, ciprofloxacin, enoxacin, trovafloxacin, gatifloxacin, etc.), sulfonamides (e.g., sulfamethoxazole, sulfanilamide, etc.), diaminopyrimidines (e.g., trimethoprim, etc.), rifampin, aminoglycosides (e.g., streptomycin, neomycin, netilmicin, tobramycin, gentamicin, amikacin, etc.), tetracyclines (e.g., tetracycline, doxycycline, demeclocycline, minocycline, etc.), spectinomycin, macrolides (e.g., erythromycin, azithromycin, clarithromycin, dirithromycin, troleandomycin, etc.), and oxazolidinones (e.g., linezolid, etc.) and (f) combinations of two or more of the foregoing.

Additional agents for use in conjunction with the scaffolds also include biopolymers including extracellular matrix components such as collagen (e.g., types I-V in desired composition, ratios or amounts), elastin, fibrin, fibronectin and laminin, and glycosaminoglycans and proteoglycans such as hyaluronic acid, chondroitin sulfate, dermatan sulfate, keratin sulfate, heparin sulfate and heparin.

Additional agents also include imaging agents such as (a) contrast agents for use in connection with x-ray fluoroscopy, including metals, metal salts and oxides (particularly bismuth salts and oxides), and iodinated compounds, among others, (b) contrast agents for use in conjunction with ultrasound imaging, including organic and inorganic echogenic particles (i.e., particles that result in an increase in the reflected ultrasonic energy) or organic and inorganic echolucent particles (i.e., particles that result in a decrease in the reflected ultrasonic energy), and (c) contrast agents for use in conjunction with magnetic resonance imaging (MRI), including contrast agents that contain elements with relatively large magnetic moment such as Gd(III), Mn(II), Fe(III) and compounds (including chelates) containing the same, such as gadolinium ion chelated with diethylenetriaminepentaacetic acid.

Additional agents (e.g., therapeutic agents, biopolymers, contrast agents, etc.) may be associated with the scaffolds in various ways, including the following, among others: (a) loaded in the interior (bulk) of the scaffolds, (b) bound to the surface of the scaffolds by covalent interactions and/or non-covalent interactions (e.g., interactions such as van der Waals forces, hydrophobic interactions and/or electrostatic interactions, for instance, charge-charge interactions, charge-dipole interactions, and dipole-dipole interactions, including hydrogen bonding), (c) applied as a coating (biostable or biodegradable) that covers all or a portion of the scaffolds, (d) loaded in surface features (e.g., depressions) in the scaffolds, and (e) combinations of the forgoing.

In various embodiments, the scaffolds contain 1 wt % or more of one or more of the preceding additional agents (e.g., from 1 wt % to 2 wt % to 5 wt % to 10 wt % to 25 wt % to 40 wt % to 50 wt % to 60 wt % to 70 wt % to 80 wt % to 90 wt % to 95 wt % to 98 wt % to 99 wt % or more).

As noted above, surgical scaffolds in accordance with the present disclosure may be provided in a wide range of shapes and sizes. A few specific embodiments of the present disclosure will now be discussed in conjunction with the drawings.

Figure 1A:
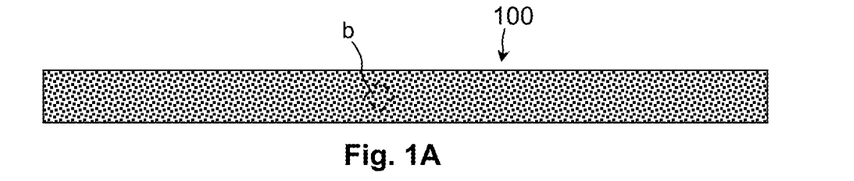
FIG. 1A is a schematic top view of a surgical scaffold, in accordance with an embodiment of the invention.
Figure 1B:
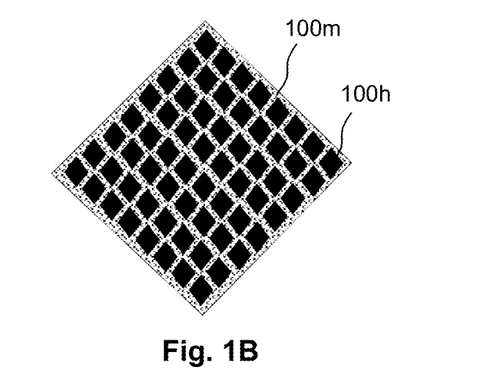
FIG. 1B is schematic expanded view of area b in FIG. 1A.
Figure 1C:
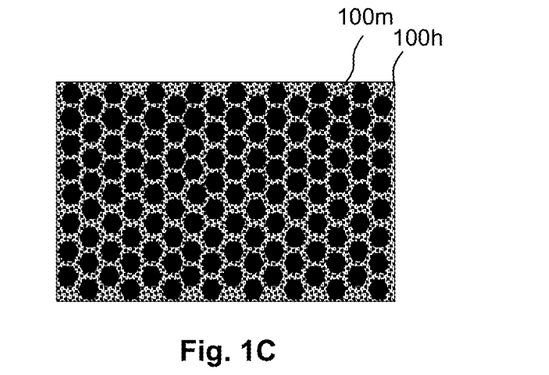
FIG. 1C is a schematic view of a portion of a scaffold with hexagonal through holes, in accordance with an embodiment of the invention.

Turning to FIG. 1A, there is schematically illustrated therein a surgical scaffold 100, which may be used, for instance, as a urethral sling. The material for the surgical scaffold 100 may comprise a uniform distribution of pores over its surface. For example, FIG. 1B is an expanded view of area b in FIG. 1A and shows a series of polygonal (diamond shaped) through-holes 100h. One characteristic of such polygonal through holes is that the material 100m remaining is of a net-like conformation, grossly resembling a mesh formed from one or more filaments, but without the crossover points, knots, and other features associated with filamentous meshes. As another example, FIG. 1C is shows a portion of a scaffold with a series of polygonal (hexagonal) through-holes 100h. Note also that material 100m remaining between the holes can have a wide variety of aspect ratios (width/thickness) with typical widths ranging from μm to mm in scale (e.g., 10 μm to 10 mm) and typical thicknesses ranging from 50 to 500 μm.

The material 100m may be provided with nano-features and/or micro-features in accordance with the invention. Typical dimensions for such a urethral sling range from 1 to 25 cm (e.g., 1 to 2 to 5 to 10 to 20 to 25 cm) in length and from 1 to 25 cm (e.g., 1 to 2 to 5 to 10 to 20 to 25 cm) in width, among other possibilities. Typical thicknesses for the urethral sling range from 50 to 500 μm. Typical dimensions for the through-holes in the scaffold range from 0.1 to 5 mm in length and width, among other possibilities. In a specific embodiment, nano-features (e.g., nano-holes) having a width, length and depth ranging from 10-1000 nm and a spacing of 10-1000 nm may be provided on one or both surfaces of the sling 100.

As previously noted, pelvic floor (pelvic support) disorders involve a dropping down (prolapse) of the bladder, rectum and/or uterus caused by weakness of or injury to the ligaments, connective tissue, and muscles of the pelvis. Pelvic floor disorders may be treated by implanting a surgical scaffold in accordance with the present disclosure within the patient's pelvis to support the organ or organs that require support.

Figure 5:
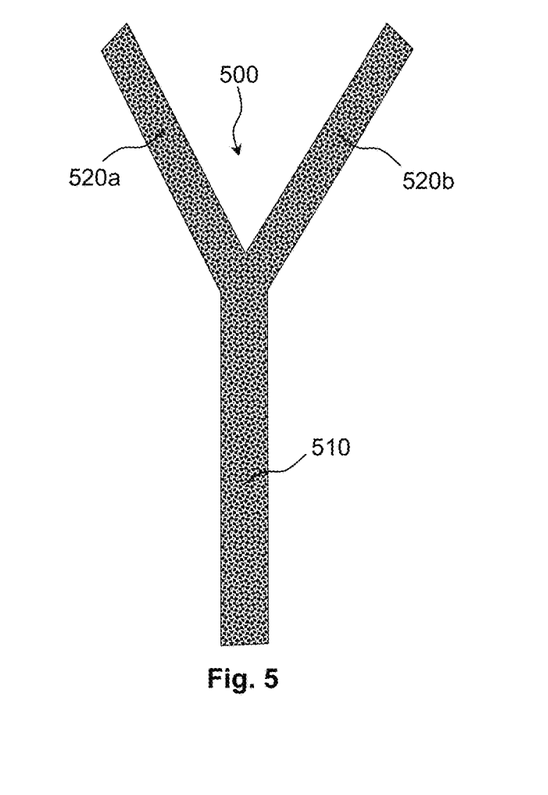
FIG. 5 is a schematic top view of a "Y" shaped surgical scaffold, in accordance with an embodiment of the invention.

In accordance with one embodiment, there is schematically illustrated in FIG. 5 a surgical scaffold 500, for example, a Y-shaped scaffold, having arms 510, 520a and 520b. (Arms 520a, 520b may be secured to the vaginal apex and arm 510 may be secured to the sacral promontory using sacrocolpopexy as is known in the art for Y-shaped meshes. The scaffold may be placed using known procedures including transvaginal or abdominal procedures.) Typical thicknesses for the scaffold 500 range from 50 to 500 μm, among other values. As with the scaffold of FIG. 1, the material for the surgical scaffold 500 comprises through-holes (not separately illustrated). Typical dimensions for the through-holes in the scaffold range from 0.5 to 5 mm in length and width, among other possibilities. In certain embodiment, nano-features (e.g., nano-depressions) having a width, length and depth ranging from 10-200 nm and a spacing ranging from 10-200 nm, among other values, may be provided on one or both surfaces of the scaffold 500.

Figure 2:
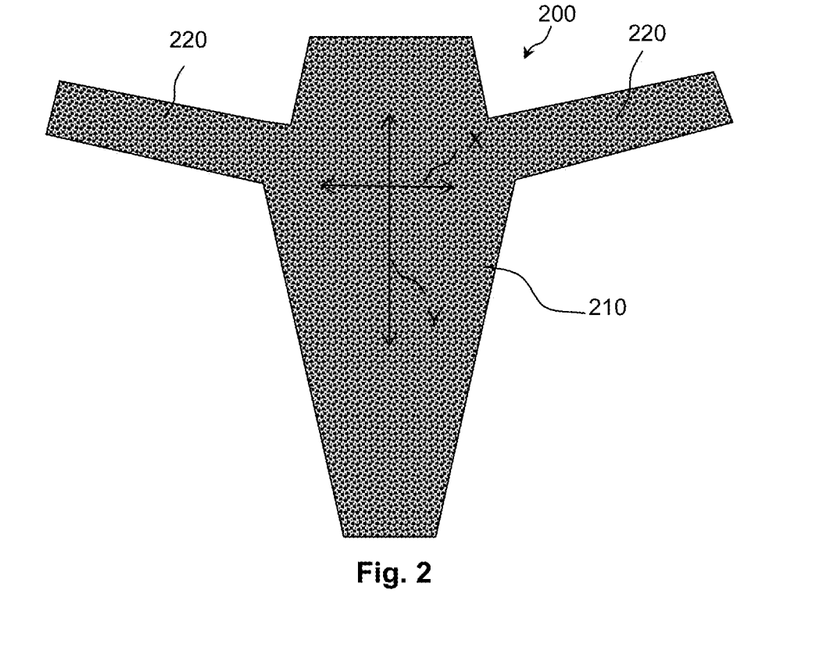
FIG. 2 is a schematic top view of a surgical scaffold which has a central body portion from which a plurality of arms emanates, in accordance with an embodiment of the invention.

In accordance with another embodiment, there is schematically illustrated in FIG. 2 a surgical scaffold 200, for example, a pelvic floor repair scaffold, having a central portion 210 and a plurality of arms 220 that emanate from the central portion 210. As used herein an "arm" is an elongated scaffold component whose length is at least two times greater than its width, typically ranging from 2 to 3 to 4 to 5 to 6 to 8 to 10 or more times the width. (In this regard, surgical sling 100 of FIG. 1 can be thought of as a single-arm device.) The central portion 210 may be used in a hammock-like fashion to support an internal organ such as the vagina, while the arms 220 may be affixed to ligaments with the pelvis (e.g., sacrospinous ligament, uterosacral ligament, sacral promontory, etc.). The scaffold may be placed using known procedures including trans-vaginal or abdominal procedures.

Typical thicknesses for the scaffold 200 range from 50 to 500 μm. As with the scaffold of FIGS. 1A-1B and 5, the material for the surgical scaffold 200 comprises through-holes (not specifically illustrated). Typical dimensions for the through-holes in the scaffold range from 0.1 to 5 mm in length and width, among other possibilities. In certain embodiment, nano-features (e.g., nano-depressions) having a width, length and depth ranging from 10-200 nm and a spacing of 10-200 nm, among other values, may be provided on one or both surfaces of the scaffold 200.

In certain embodiments, the central portion 210 has either through-holes, nano-features or both, while the arms 220 do not have through-holes, do not have nano-features or do not have both. For example, the arms 220 may be constructed of a flat continuous smooth polymer sheet without through-holes and without nano-features. Such a configuration provides the arms with greater strength while ensuring minimal adhesion to or ingrowth into surrounding tissue and organs.

With continued reference to FIG. 2, in certain embodiments, the central portion 210 has a Young's modulus along its length Y that is greater than the Young's modulus along its width X (e.g., the Young's modulus along its length Y may be >1. to 1.5 to 2 to 3 to 4 to 5 times the Young's modulus along its width X, among other values). In this regard, the central portion may have lower elongation and higher strength properties along its length Y (e.g., a Young's modulus ranging from >0.1 to 100 $N/mm^2$) and higher elongation and lower strength properties along its width X (e.g., a Young's modulus ranging from 0.1 to <100 $N/mm^2$).

In one specific embodiment, the scaffold 200 may be formed from a polyisobutylene-based polyurethane (e.g., polyurethane formed from a polyisobutylene diol as described in U.S. Pub. No. 2010/0023104 or 2010/0179298) the polymer having a material Young's modulus of about 1 to 50 $N/mm^2$ and may be about 1 to 500 μm in thickness, with rectangular or diamond shaped through holes ranging from 0.1 to 5 mm in length and width, and with nano-holes or nanofeatures of approximately 25-100 nm in length, width, depth and spacing.

Figure 3:
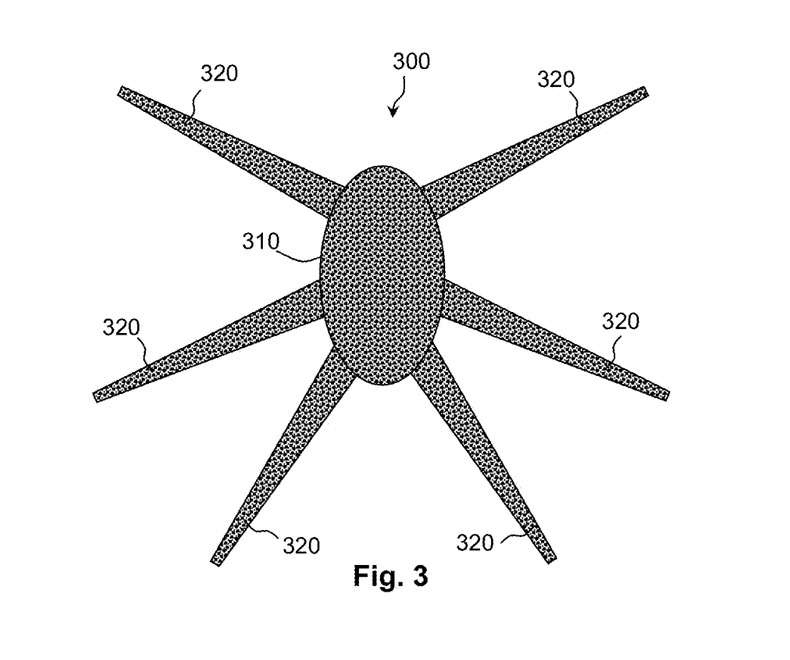
FIG. 3 is a schematic top view of a surgical scaffold which has a central body portion from which a plurality of arms emanate, in accordance with another embodiment of the invention.

Although the scaffold of FIG. 2 has two rectangular arms and a polygonal central body portion, other body and arm shapes and other numbers of arms (e.g., 3, 4, 5, 6, 7, 8, etc.) may be used. As one specific variation, FIG. 3 illustrates a scaffold 300 having a non-circular (oval) central body portion 310 and six non-rectangular (trapezoidal) arms 320, among near-limitless other possibilities.

As seen from the above, in many embodiments, a scaffold in accordance with the present disclosure may be positioned in the same fashion as biologic and synthetic grafts currently used in pelvic floor repair surgery, such that it performs the same function as currently used grafts (e.g., suspending the vaginal apex, supporting a visceral wall, etc.). However, the present disclosure is not limited to pelvic floor repair; it may be used for other soft tissue repair such as stress urinary incontinence treatment, hernia repair, repair of skeletal muscle and repair of connective tissue (e.g. tendon repair), among various other procedures in which surgical meshes are employed.

Scaffolds in accordance with the present disclosure can be formed using a variety of techniques.

For instance, scaffolds can be formed by molding processes whereby through-holes and micro-features and/or nano-features are formed using a suitable mold.

Figure 4A:
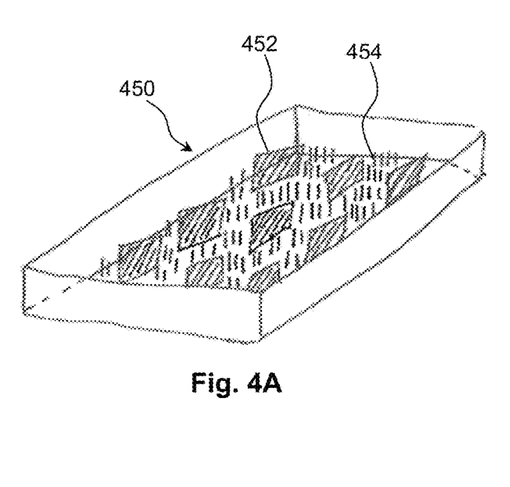
FIG. 4A is a schematic illustration of a mold for forming a surgical scaffold, in accordance with an embodiment of the invention.
Figure 4B:
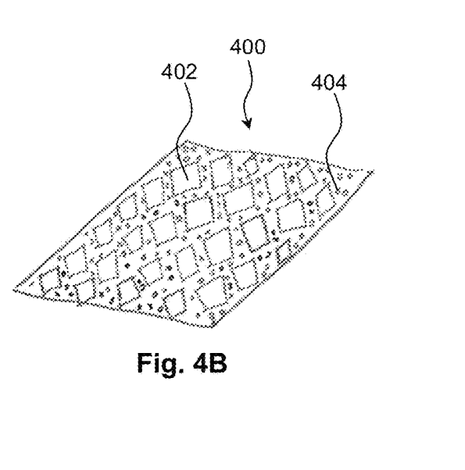
FIG. 4B is a schematic illustration of a surgical scaffold that is formed using the mold of FIG. 4A.

In a specific example, with reference to FIGS. 4A and 4B, a scaffold 400 is formed using a mold 450, which contains mm-scale diamond-shaped protrusions 452 which can be used to form mm-scale through-holes 402 in the scaffold 400 and which contains nm-scale or µm-scale columnar protrusions (pillars) 454 which can be used to form nm-scale or µm-scale blind-holes 404 in the scaffold 400. To form through-holes 402, protrusions 452 must be greater than or equal to the thickness of the resulting scaffold (e.g., µm scale) whereas the protrusions 454 must be less than the thickness of the resulting scaffold to form blind-holes 454.

Scaffolds can also be formed using fabrication processes that comprise first creating a polymer sheet of suitable thickness (e.g., by extrusion) followed by further processing (a) to provide an overall shape for the scaffold (e.g., linear, Y-shaped, body with multiple arms, etc.), (b) to provide mm-scale through-holes as described herein and (c) to provide micro-features and/or nano-features as described herein.

For example, mm-scale through-holes may be created in a previously formed polymeric material by a suitable cutting technique (e.g., die cut, laser cut, water-jet cut, cutting using metallic cutting tools, etc.).

Micro-features and/or nano-features may be provided using a suitable mold (which may be formed from a variety of metal, ceramic, polymeric, etc. metals) as previously discussed. Micro-features and/or nano-features may also be formed in a previously formed polymeric material using a variety of techniques.

In this regard, various micro- and nano-fabrication techniques are known in the semiconductor industry for depositing and etching a variety of metallic, polymeric and ceramic materials, which may be used to provide molds or previously formed polymeric materials with micro-features and/or nano-features as described herein.

Metal, polymer, or carbon nanotube or rods may be grown from or attached to a mold surface or a previously formed polymeric material surface using known techniques.

Chemical etching may be used to form nano-features in molds and previously formed polymeric materials, with depth control being achieved by adjusting the composition of the etching solution (e.g. bases, acids, organic solvents, etc. in various concentrations), and time.

Polymeric micro-features and nano-features may be formed in molds and previously formed polymeric materials by grafting polymers from a surface (e.g., a mold or extruded polymer sheet surface), for example, a gold surface+thiol or gold surface+thiol mixture may be used to create a nano-featured surface. See Whitesides et al., *Sci. Prog.* 88 (2005) 17-48.

Polymeric micro-features and nano-features may be also be formed by depositing or grafting block copolymers with hydrophilic and hydrophobic blocks onto/from a surface, wherein the block copolymer self-organizes to create micro-scale or nano-scale hydrophilic and hydrophobic phase domains. By swelling the hydrophilic domains, micro-scale or nano-scale protrusions (e.g., ridges, pillars, etc., depending to the morphology of the separated phases) may be formed. Examples of hydrophobic blocks include polystyrene, polyisobutylene and poly(methyl methacrylate) blocks, whereas examples of hydrophilic blocks including polyacrylic acid, polyethylene oxide, and polypropylene oxide blocks.

Direct write techniques (e.g., using a sharp stylus or micropen) may also be used to generate a range of features.

In other aspects of the disclosure, medical kits are provided. The medical kits may comprise any combination of two or more of the following items: (a) a sterile surgical scaffold in accordance with the present disclosure, (b) suitable packaging material and (c) printed material with one or more of the following: (i) storage information and (ii) instructions regarding how to implant the surgical scaffold in a subject.

Various aspects of the disclosure relating to the above are enumerated in the following paragraphs:

Aspect 1. A surgical scaffold for soft tissue repair, said surgical scaffold comprising a sheet of non-filamentous polymeric material, at least a portion of the sheet surface comprising a plurality of through-holes, wherein the Young's modulus of the polymeric material ranges from 0.1 to 1000 N/mm$^2$.

Aspect 2. The surgical scaffold of aspect 1, wherein said through-holes range from 0.1 mm to 5 mm in width.

Aspect 3. The surgical scaffold of any of aspects 1-2, wherein said through-holes are polygonal through-holes.

Aspect 4. The surgical scaffold of any of aspects 1-3, further comprising nano-features formed in at least a portion of the sheet surface.

Aspect 5. The surgical scaffold of aspect 4, wherein said nano-features have a width, depth and spacing between 10 nm and 500 nm.

Aspect 6. The surgical scaffold of aspect 4, wherein said nano-features are selected from nano-holes, nano-pillars, nano-ridges, nano-trenches and combinations of the same.

Aspect 7. The surgical scaffold of any of aspects 1-6, wherein said sheet ranges from 10 µm to 1 mm in thickness.

Aspect 8. The surgical scaffold of any of aspects 1-7, wherein at least a portion of said sheet is mechanically anisotropic.

Aspect 9. The surgical scaffold of aspect 8, wherein at least a portion of said sheet comprises a Young's modulus in a first direction along the sheet surface that is at least >1 times than a Young's modulus in a second direction along the sheet surface that is perpendicular to the first direction.

Aspect 10. The surgical scaffold of any of aspects 1-9, wherein said polymeric material comprises a copolymer that comprises polyisobutylene.

Aspect 11. The surgical scaffold of any of aspects 1-9, wherein said polymeric material comprises a polyurethane.

Aspect 12. The surgical scaffold of aspect 11, wherein said polyurethane comprises one or more polyisobutylene segments.

Aspect 13. The surgical scaffold of any of aspects 1-13, wherein said scaffold comprises a therapeutic agent.

Aspect 14. The surgical scaffold of aspect 13, wherein said therapeutic agent is a hormone.

Aspect 15. The surgical scaffold of any of aspects 1-14, wherein said scaffold is formed using a mold.

Aspect 16. The surgical scaffold of any of aspects 1-14, wherein the surgical scaffold is a pelvic floor repair scaffold.

Aspect 17. The surgical scaffold of any of aspects 1-16, wherein the surgical scaffold comprises a body and two or more arms extending from the body.

Aspect 18. The surgical scaffold of aspect 17, wherein said body is mechanically anisotropic.

Aspect 19. The surgical scaffold of aspect 17, wherein said body comprises said through-holes Aspect 20. The surgical scaffold of any of aspects 1-19, wherein the scaffold is sterile and is disposed in a package that maintains the sterility of the scaffold.

Aspect 21. A surgical scaffold of any of aspects 1-20 having a mass density ranging from 1 to 20 g/m$^2$.

Aspect 22. A surgical method comprising implanting the scaffold of any of aspects 1-21 into a subject.

Aspect 23. A surgical scaffold for soft tissue repair, said surgical scaffold comprising a sheet of non-filamentous polymeric material that does not shrink in a dimension perpendicular to an applied strain in a first direction along the sheet surface.

Aspect 24. A surgical scaffold for soft tissue repair, said surgical scaffold comprising a sheet of non-filamentous polymeric material, wherein the scaffold can be independently elongated in multiple directions simultaneously.

Although various embodiments are specifically illustrated and described herein, it will be appreciated that modifications and variations of the present invention are covered by the above teachings and are within the purview of any appended claims without departing from the spirit and intended scope of the invention.

The invention claimed is:

1. A medical device comprising:
a surgical scaffold for soft tissue repair, the surgical scaffold including a central portion and a first arm portion and a second arm portion extending from the central portion, the central portion configured to support a vagina of a patient,
the central portion and at least one of the first arm portion or the second arm portion being defined by a continuous sheet of non-filamentous polymeric material, the central portion including a plurality of through-holes and polymeric surface features extending substantially between the first arm portion and the second arm portion, at least one of the through-holes being between a first polymeric surface feature and a second polymeric surface feature, the first and second polymeric surface features including a plurality of trenches and ridges, the plurality of trenches and ridges including a first set of a trench and a ridge that are parallel to each other and a second set of a trench and a ridge that are parallel to each other, the first set intersecting with the second set in a cross-hatched-type pattern, the first arm portion being devoid of through-holes and being devoid of polymeric surface features,
wherein at least a portion of the sheet is mechanically anisotropic having a Young's modulus in a first direction along a sheet surface that is at least more than one time greater than a Young's modulus in a second direction along the sheet surface that is perpendicular to the first direction.

2. The medical device of claim 1, wherein the plurality of through-holes range from 0.1 mm to 5 mm in width.

3. The medical device of claim 1, wherein the central portion includes a first surface and a second surface opposite to the first surface, the second surface being separated from the first surface by a thickness of the continuous sheet of non-filamentous polymeric material at the central portion, the first surface of the central portion defining the polymeric surface features, the second surface of the central portion being devoid of polymeric surface features including trenches and ridges.

4. The medical device of claim 1, wherein the sheet of non-filamentous polymeric material ranges from 10 μm to 1 mm in thickness.

5. The medical device of claim 1, wherein the sheet of non-filamentous polymeric material includes a copolymer having polyisobutylene.

6. The medical device of claim 1, wherein the sheet of non-filamentous polymeric material includes a polyurethane.

7. The medical device of claim 6, wherein the polyurethane includes one or more polyisobutylene segments.

8. The medical device of claim 1, wherein the surgical scaffold includes a therapeutic agent and an imaging agent.

9. The medical device of claim 1, wherein each of the polymeric surface features has a dimension ranging from 1 to 1000 nanometers.

10. The medical device of claim 1, wherein the surgical scaffold is a pelvic floor repair scaffold.

11. The medical device of claim 1, wherein the at least one portion of the sheet of non-filamentous polymeric material is mechanically anisotropic by varying hole size, shape and density along the sheet surface.

12. The medical device of claim 1, wherein the surgical scaffold is sterile and is disposed in a package that maintains the sterility of the scaffold.

13. The medical device of claim 1, wherein the surgical scaffold has a mass density ranging from 1 to 20 g/m$^2$.

14. A surgical method comprising implanting the medical device of claim 1 into a subject.

15. The medical device of claim 1, wherein the Young's modulus in the first direction along the sheet surface is at least 2 times the Young's modulus in the second direction along the sheet surface.

16. The medical device of claim 1, wherein the Young's modulus in the first direction along the sheet surface ranges from 1.5 times to 5 times the Young's modulus in the second direction along the sheet surface.

17. A medical device comprising:
a surgical scaffold for soft tissue repair, the surgical scaffold including a central portion, a first arm portion extending from the central portion at a non-zero angle, and a second arm portion extending from the central portion at a non-zero angle, the central portion, the first arm portion, and the second arm portion being defined by a continuous sheet of non-filamentous polymeric material that does not shrink in a dimension perpendicular to an applied strain in a first direction along a sheet surface, wherein the central portion defines a plurality of through-holes and polymeric surface features extending substantially between the first arm portion and the second arm portion, at least one of the through-holes being between a first polymeric surface feature and a second polymeric surface feature, and each of the first arm portion and the second arm portion is constructed of a flat continuous smooth polymer sheet without through-holes and without polymeric surface features, the first and second polymeric surface features including a plurality of trenches and ridges, the plurality of trenches and ridges including a first set of a trench and a ridge that are parallel to each other and a second set of a trench and a ridge that are parallel to each other, the first set intersecting with the second set in a cross-hatched-type pattern.

\* \* \* \* \*